US008641760B2

(12) United States Patent
Mendius et al.

(10) Patent No.: US 8,641,760 B2
(45) Date of Patent: Feb. 4, 2014

(54) OSSICULAR PROSTHESIS WITH STABILIZER AND METHOD OF USE WITH INTACT STAPES

(75) Inventors: Richard W. Mendius, Collierville, TN (US); Anthony D. Prescott, Arlington, TN (US); Patrick Ireland, Cordova, TN (US)

(73) Assignee: Enteroptyx, Memphis, TN (US)

( * ) Notice: Subject to any disclaimer, the term of this patent is extended or adjusted under 35 U.S.C. 154(b) by 402 days.

(21) Appl. No.: 13/102,116

(22) Filed: May 6, 2011

(65) Prior Publication Data

US 2012/0283827 A1 Nov. 8, 2012

(51) Int. Cl.
*A61F 2/18* (2006.01)

(52) U.S. Cl.
USPC .......................................................... 623/10

(58) Field of Classification Search
USPC .......................................................... 623/10
See application file for complete search history.

(56) References Cited

U.S. PATENT DOCUMENTS

| 4,281,419 | A | 8/1981 | Treace |
| 4,597,764 | A | 7/1986 | Black |
| 4,601,723 | A | 7/1986 | McGrew |
| 4,624,672 | A | 11/1986 | Lenkauskas |
| 4,655,776 | A | 4/1987 | Lesinski |
| 4,740,209 | A | 4/1988 | Gersdorff |
| 5,370,689 | A | 12/1994 | Causse |
| 6,168,625 | B1 | 1/2001 | Prescott |
| 6,203,571 | B1 | 3/2001 | Magnan et al. |
| 7,553,328 | B2 | 6/2009 | Steinhardt et al. |
| 2001/0027342 | A1 | 10/2001 | Dormer |
| 2002/0095063 | A1 | 7/2002 | Kroll et al. |
| 2004/0162614 | A1 | 8/2004 | Steinhardt et al. |
| 2007/0055372 | A1 | 3/2007 | Prescott et al. |
| 2009/0164010 | A1 | 6/2009 | Steinhardt et al. |
| 2009/0240330 | A1 | 9/2009 | Steinhardt et al. |
| 2009/0240331 | A1 | 9/2009 | Steinhardt et al. |
| 2011/0054607 | A1* | 3/2011 | Reitan et al. ................... 623/10 |
| 2012/0123538 | A1* | 5/2012 | Kraus ............................ 623/10 |
| 2012/0197394 | A1* | 8/2012 | Vincent et al. ................ 623/10 |
| 2012/0283827 | A1 | 11/2012 | Mendius et al. |

FOREIGN PATENT DOCUMENTS

| EP | 1430855 | 6/2004 |
| WO | WO2011040977 | 4/2011 |
| WO | WO2012/154404 | 11/2012 |

OTHER PUBLICATIONS

Atlas of Middle Ear Surgery, M. Gersdorff, Hean-Marc Gerard, Thieme 2011.
Medtronic ENT International Product Catalog 2010-2011, © 2009, Medtronic Inc. LIT897142 REV1.
Ossiculoplasty with Intact Stapes and Absent Malleus: The Silastic Banding Technique, Robert Vincent et al., Otology and Neurology 26:846-852, 2005.

* cited by examiner

*Primary Examiner* — Suzette J Gherbi
(74) *Attorney, Agent, or Firm* — Gordon & Jacobson, PC

(57) ABSTRACT

A system is provided for stabilized total ossicular replacement in a middle ear having an intact stapes with a capitulum and a footplate. The system includes an ossicular replacement prosthesis including with elongate shaft and a head coupled to the shaft, and a stabilizer that couples the prosthesis to the stapes. The stabilizer has a first portion with a first opening and a second portion with a second opening, said first opening sized to stably engage the shaft of the prosthesis, and said second opening sized to stably engage the capitulum. When the shaft and capitulum are engaged they are retained in an side-by side configuration. The stabilizer may be constructed of an elastic polymer, an elastic metal alloy, a plastic material or a shape memory material.

23 Claims, 3 Drawing Sheets

OSSICULAR PROSTHESIS WITH STABILIZER AND METHOD OF USE WITH INTACT STAPES

BACKGROUND OF THE INVENTION

1. Field of the Invention

The present invention relates to prostheses. More particularly, the invention relates to ossicular prostheses, and specifically to total ossicular prostheses.

2. State of the Art

Hearing is facilitated by the tympanic membrane transforming sound in the form of acoustic sound waves within the outer ear into mechanical vibrations through the chain of ossicular bones (malleus, incus, stapes) in the middle ear. These vibrations are transmitted through the ossicular bones to the footplate of the stapes where micro or macro motion of this structure results in compression waves within the fluid of the inner ear. These compression waves lead to vibrations of the cilia (hair cells) located within the cochlear where they are translated into nerve impulses. The nerve impulses are sent to the brain via the cochlear nerve and are interpreted in the brain as sound.

Hearing efficiency can be lost to erosion of the ossicular bones. Various combinations or portions of the bones can be replaced. For example, the malleus and incus can be together replaced in a manner that leaves all or a portion of the stapes intact. Such a prosthesis is a partial ossicular replacement prosthesis, or PORP, and extends between the tympanic membrane and the stapes capitulum. A PORP provides relative stability as the prosthesis is stabilized on an intact portion of a remaining ossicle. Alternatively, the incus, malleus and stapes can all be completely replaced or bypassed by a total ossicular replacement prosthesis, or TORP, that extends from the tympanic membrane to the stapes footplate located over the oval window. Referring to Prior Art FIGS. 1 and 2, a TORP 10 as generally described in U.S. Pat. No. 6,618,625 is shown. The TORP 10 includes a head 12 for placement against the tympanic membrane and an adjustable length shaft 14 that extends from the head to the remnant footplate 16 of the stapes 18. The shaft 14 preferably includes alternating enlarged and reduced diameter portions 20*a*, 20*b* for adjustable engagement with a sleeve 22 in the head 12, and an enlarged base or foot 24 for increased support on the footplate 16. In addition, the head 12 may include a malleus arm 26 to provide some upper support for the prosthesis 10 relative to a remnant of a non-functional malleus. Nevertheless, the TORP 10 is inherently unstable as a result of the forces F1-F5 to which it is subject.

In order to overcome the instability of a different type of TORP, i.e., a fixed length prosthesis with a smooth shaft, it has been proposed that, when the stapes 18 remains intact, the shaft of the TORP be stabilized against the capitulum 28 (i.e., the upper cap of the stapes arching structure). See Vincent, R. et al., Ossiculoplasty with Intact Stapes and Absent Malleus: The Silastic Banding Technique, *Otology & Neurotology*, 26: 846-852 (2005). In the Vincent study, a silastic disk was cut and then a central hole was punched therethrough to define a circular band sized to fit snugly about the neck of the capitulum of an intact stapes. The band was placed about the capitulum and as the TORP is inserted into the middle ear for implantation, the band is stretched and the shaft of the TORP is introduced within the stretched opening. The TORP is moved into final implantation position, with its inferior surface resting on the center of the footplate, and the band is then released against the shaft against the stapes. There are significant challenges to positioning the band about the capitulum and TORP shaft in a manner that properly restrains the TORP to provide the desired stabilization, and which also prevents damage to the tendon of the stapedius muscle extending from adjacent the capitulum. In addition, it is difficult to expand the band to accommodate receiving the larger foot-end of the shaft during the implantation procedure.

SUMMARY OF THE INVENTION

In accord with the invention, a total ossicular prosthesis is used in conjunction with an improved stabilizer that stabilizes the prosthesis relative to an intact stapes. The ossicular prosthesis preferably is an adjustable length prosthesis having a head and an elongate shaft. The head is formed for contacting a tympanic membrane when implanted in a middle ear of a human. The elongate shaft preferably has an alternating portions of reduced and enlarged diameter. The shaft is preferably moveably joined relative to the head, allowing the effective length of the prosthesis to be adjusted by axial movement of the shaft relative to the head. The joining of the shaft to the head allows the head to grip the shaft under static and anatomic forces. The distal end of the shaft may include a base of larger diameter to increase surface area contact, and thus stability, on the stapes footplate.

The stabilizer of the invention includes a first portion defining a first opening that grips the shaft of the prosthesis, and a second portion defining a second opening that grips the capitulum of the stapes. The first opening for the shaft is relatively smaller than the second opening, and preferably sized to lockingly engage the reduced diameter portion of the shaft so that when engaged thereabout the first portion is substantially fixed in longitudinal displacement along the shaft. The larger opening is preferably at least twice the diameter of the smaller opening and is sized to lockingly engage about the capitulum. The first and second openings may be defined by complete uninterrupted circles or other closed shapes, or lateral entrances may be defined into one or both of the openings such that the stabilizer may be laterally positioned onto the shaft and capitulum. The stabilizer may be made of an elastic material, such as silicone or another silastic. Alternatively, the stabilizer may be made of an elastic but more rigid material such as Nitinol metal alloy, which can be resiliently opened relative to a respective lateral entrance of an opening to accommodate placement of the stabilizer on the shaft or capitulum. As yet another alternative, a relatively inelastic material, such as titanium, can be used which can be formed with an entrance sized to accommodate the prosthesis shaft or stapes capitulum, and then crimped closed about the respective structure. Further, a heat-activated shape memory alloy may be used to close openings about the prosthesis shaft or capitulum once the structure is extended thereabout.

In one embodiment of using an elastic stabilizer with openings defined by closed shapes, the first portion with the smaller first opening of the stabilizer is initially positioned on the shaft of the TORP, between the head and the base, securely engaging one of the reduced diameter portions of the shaft so as to be locked in longitudinal position along the shaft. The shaft of the TORP is then adjusted in axial position relative to the head of the TORP, and any portion of the adjusted shaft protruding from the head is preferably excised from the prosthesis by cutting. The TORP is inserted into the middle ear, and the second portion of the stabilizer with the larger second opening is expanded over the capitulum and released to lock thereabout. Then, if needed, a tool can be used to expand the first opening or otherwise force and resiliently deform first portion along the shaft to accommodate movement of the first portion along the shaft such that when released it lockingly resides in a different reduced diameter portion of the shaft.

In an embodiment of using a stabilizer having first and second openings with lateral entrances thereinto, the second portion of the stabilizer with the larger second opening is initially manipulated to force open the second opening at its lateral entrance. Once the second portion is advanced over the capitulum, the second opening closes about the capitulum to lock in place onto the stapes. The TORP is then introduced into middle ear. Assuming the TORP is properly adjusted in length (if not it can be removed and properly adjusted), the TORP is laterally inserted into the first opening of the first portion of the stabilizer to force open the first portion so that the first portion receives the shaft of the TORP, with the first portion lockingly engaging in a reduced diameter portion of the shaft.

In one embodiment of using a stabilizer with one of the first and second openings defined by a close shape and the other defined by a shape with lateral entrance therein, it is appreciated that a combination of the techniques described above can be used to attach the stabilizer to the shaft of the TORP and the capitulum, each being received in a respective opening of the stabilizer.

It is appreciated that in each embodiment, the shaft of the TORP is stabilized against the intact stapes, specifically at the capitulum. Further, because the shaft has alternating reduced and enlarged portions, the exact point at which the shaft is stabilized relative to the capitulum can be determined and set.

BRIEF DESCRIPTION OF THE DRAWINGS

Prior art

Prior Art

DETAILED DESCRIPTION OF THE PREFERRED EMBODIMENTS

Figure 4:
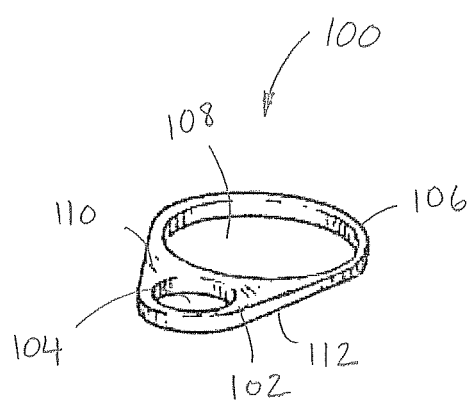
FIG. 4 is a perspective view of the TORP stabilizer of FIG. 3.
Figure 5:
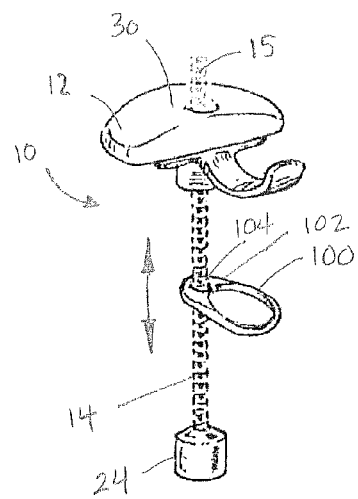
FIGS. 5-7 illustrate the method of implanting a TORP with the first embodiment of the stabilizer.
Figure 6:
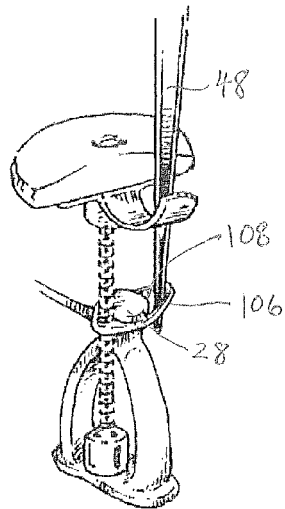
Figure 7:
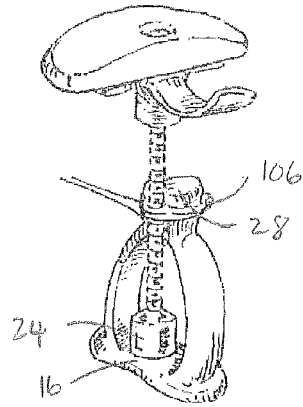

A system according to the invention includes a prosthesis stabilizer 100 (shown in FIGS. 3 and 4) for use in association with a total ossicular replacement prosthesis 10 (TORP) (as shown in FIGS. 5-7).

Figure 1:
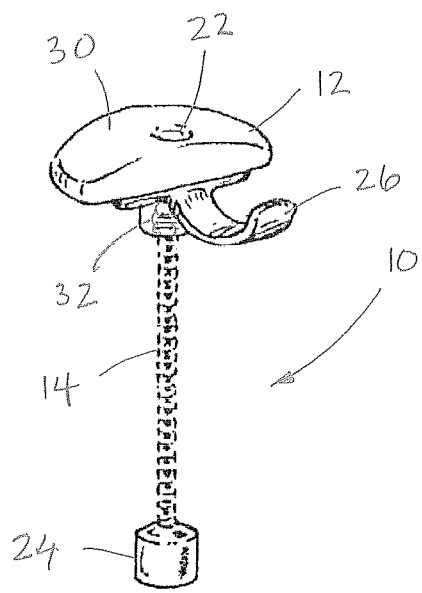
FIG. 1 illustrates a prior art TORP for use in middle ear ossicular replacement.
Figure 2:
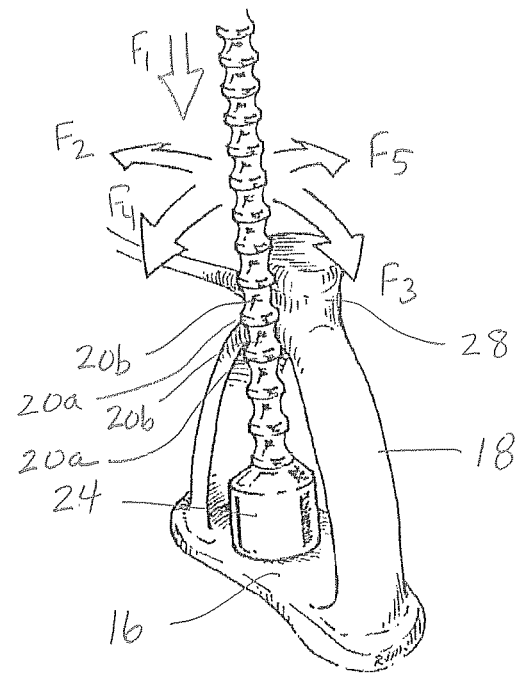
FIG. 2 shows a non-stabilized shaft of the TORP seated on a footplate of an intact stapes.

One suitable and preferred type of TORP is described in U.S. Pat. No. 6,618,625, which is hereby incorporated by reference herein and substantially similar to the TORP shown as Prior Art FIGS. 1 and 2, with the following reference numerals referring back to such figures as well as FIG. 5. The TORP 10 has a head 12 and an elongate shaft 14. The head 12 is preferably manually longitudinally displaceable along a length of the shaft 14 (in the direction of the arrows in FIG. 5) and then set in a fixed location along the shaft for implantation. The shaft 14 has a first end 15, an opposite enlarged base end 24, and a series of alternating portions of reduced and enlarged diameters, 20a, 20b, respectively, along a portion of its length between the first and base ends 15, 24. Each of the reduced diameter portions 20a has a respective smaller common diameter, and each of the enlarged diameter portions 20b has a respective larger common diameter. The head 14 of the TORP includes a surface 30 for contacting the tympanic membrane, and a resiliently deformable sleeve 22 through which the shaft 14 extends. The sleeve 22 includes a negative space 32 corresponding to the outer shape of the alternating portions 20a, 20b of the shaft 14. The sleeve 22 fixes the longitudinal position of the head 12 along the shaft 14 under static and anatomical forces; however, when the head 12 and shaft 14 are subject to sufficient manual force, the head 12 can be displaced along the shaft 14 for adjustment prior to implantation.

Figure 3:
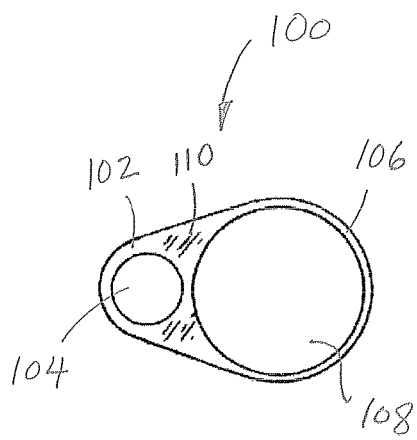
FIG. 3 is a plan view of a first embodiment of a TORP stabilizer according to the invention.

Turning to FIGS. 3 and 4, the stabilizer 100 includes a first portion 102 defining a first opening 104, and a second portion 106 defining a second opening 108. The first opening 104 is preferably circular and sized to closely engage a portion of the TORP shaft about its circumference at one of the reduced diameter portions 20a. That is, the first opening 104 substantially corresponds in diameter (i.e., within ±5%) to the common diameter of the reduced diameter portions 20a, e.g., 0.21 mm. The first opening 104 may be provided in a shape other than circular. In accord with a preferred aspect of the stabilizer, the shape and size of the first opening is adapted to contact the cylindrical shaft at three circumferential locations which are spaced at least more than 180° about the shaft of the TORP; i.e., such that the first portion 102 at the first opening 104 provides more than mere contact against the shaft, but can, in fact, securely capture the TORP shaft independent of capturing the capitulum. In this embodiment, the entire circumference of the shaft of the TORP is contacted and engaged.

The larger second opening 108 is preferably circular and preferably sized to lockingly engage about the capitulum of a stapes. The second opening 108 may be provided in a shape other than circular. The larger opening 108 has a second diameter preferably at least twice the diameter of the first opening 104, and most preferably substantially corresponds (i.e., within ±20%) in diameter to the diameter of a standard capitulum, e.g., 1.14 mm; although dedicated sizes of stabilizers each to accommodate a specific size of stapes capitulum can be provided. In accord with a preferred aspect of the stabilizer, the shape and size of the second opening is adapted to contact the capitulum at three circumferential locations which are spaced at least more than 180° about the capitulum; i.e., such that the second portion 106 at the second opening 108 provides more than mere contact against the capitulum, but can, in fact, securely capture the capitulum independent of capturing the TORP shaft. In this embodiment, the entire circumference of the capitulum is contacted and engaged.

The stabilizer 100 is in the form of a thin sheet of material, preferably 0.10 mm to 0.15 mm, and more preferably 0.127 mm, with flat upper and lower surfaces 110, 112. The stabilizer is preferably molded, rather than punched. The first and second openings 104, 108 are preferably located side-by-side, and the peripheral shape of the stabilizer preferably conforms to a smooth shape extending about the first and second openings, resulting in a pear shape device. Other shapes can be used as well.

In accord with one embodiment, the stabilizer 100 is made from an elastic polymeric material, such as silicone or another silastic material. As described below, the elastic properties of the device is used as a means to permit access to the closed shape holes for the shaft of the TORP and the capitulum. One preferred manner of using an elastic stabilizer with closed shape openings is described as follows. Referring to FIG. 5, the head 12 of the TORP 10 is removed from its shaft 14 (by axially drawing the head off the first end 15 of the shaft 14), and the first portion 102 of the stabilizer 100 with the smaller first opening 104 is advanced onto the first end 15 of the shaft 14. As the enlarged diameter portions 20b (see FIG. 2) along the shaft 14 are smaller than the first opening 102, force is applied to resiliently deform the first portion 102 so that the stabilizer can be longitudinally displaced to an anticipated location suitable for implantation. The head 12 is reattached to the shaft 14. The above steps may be performed during assembly of the TORP at a manufacturing facility or in a surgical preparation room by a technician or in the operating room by the surgeon or an assistant. Still referring to FIG. 5, during the surgical procedure, the length of the required prosthesis is determined by measuring the middle ear anatomy (the determined length of the prosthesis may be exactly as measured at the anatomy or a known or determined offset from the measurement taken) and, if necessary, the head 12 is moved along the shaft 14 by application of sufficient manual force to cause such displacement to adjust the TORP to have the determined length between the surface 30 of the head 12 and the base 24 of the shaft 14. As shown in FIG. 5, in certain cases, the first end 15 of the shaft 14 will protrude from the head 12, which is then excised from the prosthesis by cutting the shaft flush with the surface 30 of the head or even slightly recessed below the surface of the head. Depending on the adjustment in length, the stabilizer 100 may be adjusted along the length of the shaft 14 outside the patient to generally be longitudinally displaced from the base end 24 of the shaft a distance corresponding to a measured distance from the patient's stapes footplate to the patient's capitulum or may be initially set at a standard distance from the base end corresponding to a standard or average such distance, e.g., 4.0 mm.

Figure 8:
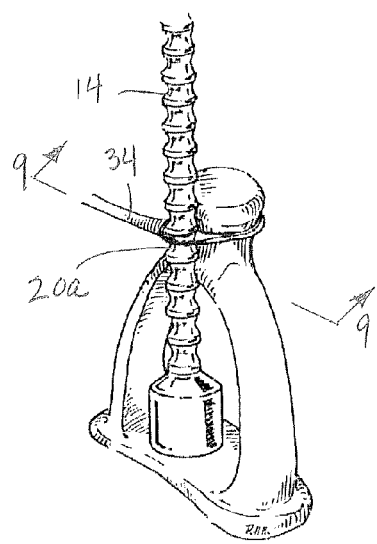
FIG. 8 illustrates the implanted TORP with the first embodiment of the stabilizer.
Figure 9:
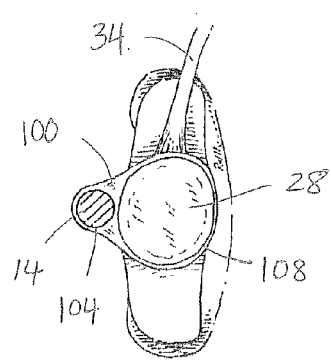
FIG. 9 illustrates a section view across line 9-9 in FIG. 8.

Referring now to FIG. 6, the TORP 10 with stabilizer 100 attached thereto is inserted and implanted into the middle ear, and the second portion 106 of the stabilizer with the larger second opening 108 is expanded with a tool such as a probe 48 or forceps and extended over the capitulum 28 and then released to engage thereabout (as shown in FIG. 7). Then, if final adjustment is required needed, the first portion 102 of stabilizer 100 can be engaged by the probe or forceps and forced along the shaft 14, e.g., by using a into a different reduced diameter portion 20a of the shaft 14 so that the base end 24 of the shaft stably rests on the footplate 16. Referring to FIGS. 8 and 9, it is clearly seen that the stabilizer 100 grips the entire circumference of each of the TORP shaft 14 and the capitulum. It is further seen that implanted stabilizer 100 holds the shaft 14 of the TORP securely relative to the stapes, and that the manner in which the first opening 104 engages a reduced diameter portion 20a prevents the shaft 14 from longitudinal movement relative to the stabilizer 100 and longitudinal displacement relative stapes 18. Moreover, the small profile and manner of attachment self-orients the stabilizer in the preferred orientation such that the stabilizer does not interfere with the tendon 34 of the stapedius muscle.

Figure 10:
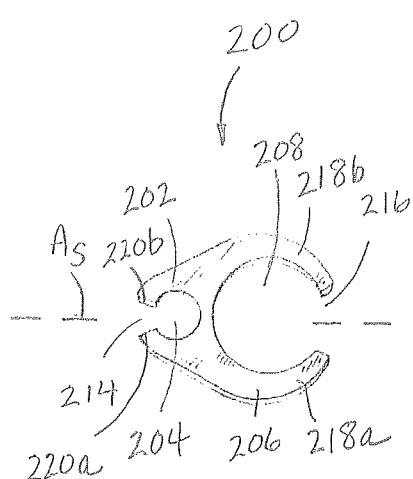
FIG. 10 is a plan view of a second embodiment of a TORP stabilizer according to the invention.

Referring now to FIG. 10, another embodiment of a stabilizer 200 for use with a TORP 10 is shown. The stabilizer 200 may be made from either a resilient polymeric material, an elastic metal alloy, such as Nitinol, or a relatively inelastic or even plastically deformable material such as titanium. The stabilizer 200 has a first portion 202 defining a first opening 204 and a second portion 206 with a second opening 208. A first lateral entrance 214 is provided through the first portion 202 into the first opening 204. The lateral entrance 214 is smaller than the diameter of the first opening 204 and smaller than the diameter of the capitulum. A second lateral entrance 216 is provided through the second portion 206 into the second opening 208. The second opening is sized for stably engaging the capitulum 28 and/or an upper portion of the cruz 29 of the stapes, as each of these anatomical features is substantially similar in diameter (see FIG. 11). Preferably the first and second lateral entrances 214, 216 are located at opposite ends of the stabilizer 200 and along the longitudinal axis $A_s$ of the stabilizer.

The lateral entrances into the openings define arms about the first and second portions. By way of example, with respect to the second entrance 216, arms 218a, 218b are defined which, depending on the material of the stabilizer, may either be resiliently flexed, plastically deformed, or otherwise manipulated or acted upon to allow the capitulum to be entered into the second opening, and then configured for captured of the capitulum. Similar structure can be provided at the first entrance 214. Such other action may include construction of the stabilizer from a heat-activatable shape memory alloy, forming the arms into an open configuration, and then applying heat to close the arms about the respective structure. Alternatively, the arms may be formed open and then plastically deformed closed about the respective structure using surgical tools. Whether the arms are resiliently flexible, are heat activatable to close, or are plastically deformable closed by tools, the respective structure of each can be used as a means to permit providing the respective first and second portions of the stabilizer about the TORP shaft and stapes.

Figure 11:
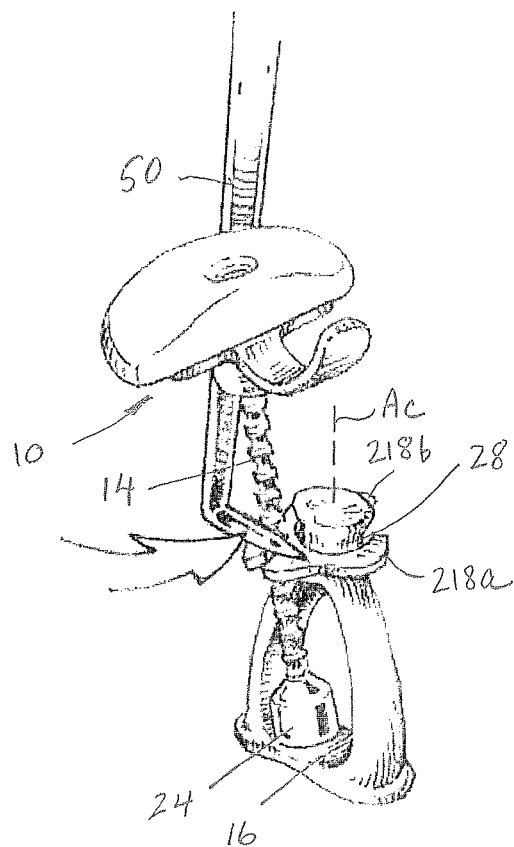
FIG. 11 is a perspective view of a third embodiment of a TORP stabilizer according to the invention.
Figure 12:
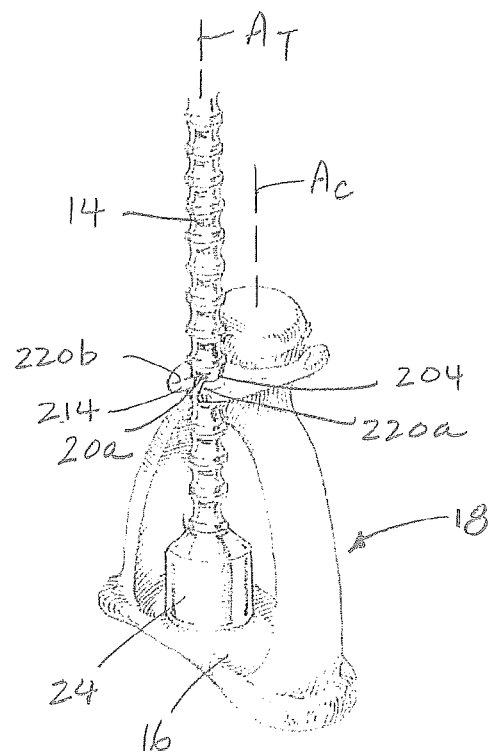

Turning to FIGS. 11 and 12, the stabilizer 200 is may be used as follows. By way of example only, use of the stabilizer 200 is described with respect to a structure having resiliently flexible arms; however, it is recognized that various steps would be appropriately modified for use with a heat-activatable shape memory material, such as a shape memory metal alloy or shape memory polymer, or a plastically deformable material. In use, the stabilizer 200 is grasped with a forceps 50 and advanced onto the capitulum 28. The two arms 218a, 218b are forced and flexed over the capitulum 28 in a direction substantially perpendicular to the axis $A_c$ through the capitulum, or by forcing at least one of the arms 218b temporarily into a configuration in which it is out-of-plane with the remainder of the stabilizer. Such action permits the arms 218a, 218b to be sufficiently opened to extend about the capitulum 28. Once the force is removed, the arms 218a, 218b return toward their initial configuration and lockingly engaged about the capitulum.

The stabilizer may alternately be engaged on the upper portion of the cruz of the stapes. For such an engagement, the stabilizer may be formed with a contour to orient the first opening 204 for receiving the shaft of the TORP in the desired orientation.

The TORP 10 is then introduced into middle ear. Assuming the TORP 10 is properly adjusted in length--if not it can be removed and properly adjusted as discussed above—the TORP is oriented at an angle (as shown in FIG. 11), the base 24 of the TORP is positioned on the footplate 16, and the shaft 14 is rotated upright on the footplate in the direction shown by the arrow and forced into the lateral entrance 214 of the first opening 204 of the first portion 202 (i.e., by resiliently deforming the arms thereof to permit the shaft 14 to enter therein) until the shaft 14 is substantially upright and a reduced diameter portion 20a of the shaft is lockingly engaged by the first portion 202 (as shown in FIG. 12). In the implanted configuration, the shaft axis $A_T$ and the capitulum axis $A_C$ are laterally offset but substantially parallel. Each of the first and second lateral entrances 214, 216 may include beveled or angled surfaces, such as 220a, 220b, to facilitate introduction of the respective elements therein.

Figure 13:
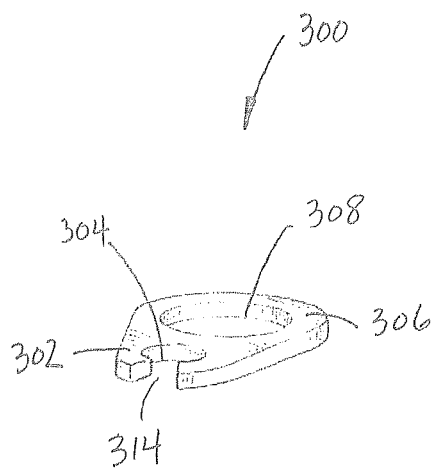
FIGS. 12 and 13 illustrate the method of implanting a TORP with the second embodiment of the stabilizer.

Referring now to FIG. 13, another embodiment of the stabilizer 300 is shown. With stabilizer 300, the first opening 304 has a lateral entrance 314 thereinto, whereas the second opening 308 is a closed shape. It is appreciated that a combination of the techniques described above can be used to attach the stabilizer 300 to the shaft 14 of the TORP 10 and the capitulum 28, each being received in its respective opening of the stabilizer. For example, the second portion 306 can first be attached the capitulum 28, and then the TORP introduced into the middle ear and attached to the first portion 302 of the stabilizer to coupled to the TORP 10 relative to the stapes 18. Alternatively, the 'inverse' device can be used wherein the first opening is a closed shape and the second opening has a lateral entrance. With such a device, the stabilizer is attached to the shaft of the TORP prior to introducing the TORP into the middle ear, and then the forceps is used to manipulate the stabilizer on the capitulum. Stabilizer 300 is preferably made of a resilient polymeric material, but may be made of other materials or a combination of materials suitable for the structure.

There have been described and illustrated herein embodiments of a stabilizer for a TORP and methods of implanting the same. While particular embodiments of the invention have been described, it is not intended that the invention be limited thereto, as it is intended that the invention be as broad in scope as the art will allow and that the specification be read likewise. Therefore, while a longitudinally adjustable TORP has been disclosed, in which the head is displaceable along the shaft of the TORP at a joint defined by a sleeve, it is appreciated that a different joint between the head and the shaft can be alternatively or additionally used. By way of example, a universal or other joint can be provided permitting the head to angularly displaced relative to the axis of the shaft. Furthermore, it is also within the scope of the invention to use the stabilizer with a TORP that is non-adjustable in length, but which preferably, though not by limitation, has a shaft with alternating portions of enlarged and reduced diameter so that the first opening can be fixed within a respective one of the reduced diameter portions. Also, the stabilizer can be used with a shaft having a relatively smooth outer surface; i.e., with a substantially common outer diameter along the majority of its length. Moreover, while all of the stabilizers are shown with a relatively common overall shape, it is appreciated that other shapes may be used. In addition, while a stabilizer has been particularly described with respect to connecting a TORP to a stapes capitulum, it is appreciated that the stabilizer may be used as a connector for stabilizing or securing other types of ossicular implants to the stapes or other middle ear structure. For that purpose, the implant may include alternate middle ear engagement structure besides a head for contacting the tympanic membrane. By way of example and not limitation, such alternative engagement structure may include a clip to engage, e.g., a portion of the malleus or incus, or a bucket with handle to engage, e.g., a portion of the incus. It will therefore be appreciated by those skilled in the art that yet other modifications could be made to the provided invention without deviating from its spirit and scope as claimed.

What is claimed is:

1. A method of implanting an ossicular replacement prosthesis into the middle ear, the prosthesis having an elongate shaft with a first circumference, the shaft having first and second ends, the middle ear having an intact stapes with an upper portion having a larger second circumference, the method comprising:

providing a prosthesis stabilizer;

engaging with the stabilizer at at least three locations at least 180° apart on the second circumference of the upper portion of the stapes; and on the shaft, engaging with the stabilizer at at least three locations at least 180° apart on the first circumference of the shaft of the prosthesis, wherein when both the upper portion of the stapes and the shaft of the prosthesis are engaged, the shaft is engaged in contact with the middle ear at its first and second ends, and the shaft is coupled relative to the upper portion of the stapes through the stabilizer.

2. A method according to claim 1, wherein the shaft is engaged prior to engaging the stapes.

3. A method according to claim 1, wherein the shaft is engaged while the prosthesis is located outside the middle ear.

4. A method according to claim 1, wherein each of the shaft and the upper portion of the stapes are engaged in respective first and second openings of a stabilizer, the first opening receiving the shaft being smaller than the second opening receiving the upper portion of the stapes.

5. A method according to claim 1, wherein the upper portion of the stapes is the capitulum.

6. A method according to claim 1, wherein the upper portion of the stapes is an upper portion of the cruz.

7. A method according to claim 1, wherein the stabilizer is made from a heat-activated shape memory material, and at least one of said engaging steps comprises heating a portion of the stabilizer.

8. A method of implanting an ossicular replacement prosthesis into the middle ear, the prosthesis having an elongate shaft with a circumference, the middle ear having a stapes, the method comprising:

providing a prosthesis stabilizer having first and second openings;

engaging a portion of the circumference of an upper portion of the stapes in the first opening of a stabilizer; and engaging a portion of the circumference of the shaft of the prosthesis in the second opening of the stabilizer such that the shaft and the stapes are stabilized relative to each other.

9. A method according to claim 8, wherein the first opening of the stabilizer engages the capitulum of the stapes.

10. A method according to claim 8, wherein the first opening is smaller than the second opening.

11. A method according to claim 8, wherein the shaft is engaged in the first portion of the stabilizer prior to engaging the upper portion of the stapes.

12. A method according to claim 8, wherein the shaft is engaged in the first portion of the stabilizer while the prosthesis is located outside the middle ear.

13. A method according to claim 8, wherein the stabilizer is made from a heat-activated shape memory material, and at least one of said engaging steps comprises heating a portion of the stabilizer.

14. A method of implanting an ossicular replacement prosthesis in a middle ear having an intact stapes with an upper portion including a capitulum and a lower footplate, the middle ear also having a tympanic membrane, said method comprising:

a) providing an ossicular replacement prosthesis including,
  i) an elongate shaft having a first end and a second end defining a base, and
  ii) a middle ear engaging structure coupled to said first end of said shaft;

b) providing a stabilizer having a first portion with a first opening and a second portion with a second opening;

c) implanting said prosthesis such that said shaft and capitulum are in a side-by side implanted configuration with said base of said shaft situated on the footplate of the stapes and said middle ear engaging structure engaged relative to the tympanic membrane; and d) engaging said stabilizer at said first opening to a portion of said shaft between said first and second ends, and engaging said stabilizer at said second opening to the upper portion of the stapes, such that said stabilizer is operably coupled to retain said shaft of said prosthesis within said first opening and the upper portion of the stapes within said second opening.

15. A method according to claim 14, further comprising:
before implanting, longitudinally displacing said middle ear engagement structure relative to said base to adjust a functional length of said prosthesis for implantation between the footplate and the tympanic membrane.

16. A method according to claim 15, wherein said shaft of said prosthesis includes a series of alternating reduced and enlarged diameter portions between said first and second ends, each of said enlarged diameter portions having a first common diameter, and each of said reduced diameter portions having a smaller second common diameter, and said middle ear engagement structure is longitudinally displaced along said series of alternating reduced and enlarged diameter portions.

17. A method according to claim 16, wherein said first opening of said stabilizer is sized to stably engage one of said reduced diameter portions of said shaft.

18. A method according to claim 17, wherein said second opening is at least twice a size of said first opening.

19. A method according to claim 18, wherein said first opening has a diameter that is substantially equal to said second common diameter.

20. A method according to claim 14, wherein both of said first and second openings are defining by closed shapes.

21. A method according to claim 20, wherein said first opening of said stabilizer is engaged onto shaft before said shaft is implanted into the middle ear.

22. A method according to claim 14, wherein said first opening of said stabilizer is engaged relative to said shaft before said shaft is implanted into the middle ear.

23. A method according to claim 14, wherein said first opening of said stabilizer is engaged relative to said shaft after said shaft is implanted into the middle ear.

\* \* \* \* \*